(12) United States Patent
Prior Ortega et al.

(10) Patent No.: US 11,833,250 B2
(45) Date of Patent: Dec. 5, 2023

(54) FOSFOMYCIN TABLET FORMULATIONS

(71) Applicant: Labiana Health, S.L., Madrid (ES)

(72) Inventors: Marta Prior Ortega, Corbera de Llobregat (ES); Ramon Francesch Ollé, Terrassa (ES)

(73) Assignee: LABIANA HEALTH, S.L., Madrid (ES)

( * ) Notice: Subject to any disclaimer, the term of this patent is extended or adjusted under 35 U.S.C. 154(b) by 0 days.

(21) Appl. No.: 17/668,146

(22) Filed: Feb. 9, 2022

(65) Prior Publication Data

US 2022/0387329 A1 Dec. 8, 2022

(30) Foreign Application Priority Data

Feb. 10, 2021 (EP) .................... 21382104

(51) Int. Cl.
*A61K 9/20* (2006.01)
*A61K 9/00* (2006.01)
*A61K 31/665* (2006.01)

(52) U.S. Cl.
CPC .......... *A61K 9/2054* (2013.01); *A61K 9/0053* (2013.01); *A61K 9/2009* (2013.01); *A61K 9/2013* (2013.01); *A61K 9/2072* (2013.01); *A61K 9/2095* (2013.01); *A61K 31/665* (2013.01)

(58) Field of Classification Search
CPC .. A61K 9/2054; A61K 9/0053; A61K 9/2009; A61K 9/2013; A61K 9/2072; A61K 9/2095; A61K 31/665
USPC ......................................................... 514/99
See application file for complete search history.

(56) References Cited

U.S. PATENT DOCUMENTS 7,303,755 B2 12/2007 Rampoldi et al.
8,604,078 B2 12/2013 Picornell Darder
8,632,818 B2 1/2014 Thoorens et al.

FOREIGN PATENT DOCUMENTS

EP 1 747 781 B1 2/2010
EP 2 656 846 B1 3/2016
ES 2 224 869 B1 7/2007
IT 1348011 B1 4/2003

OTHER PUBLICATIONS

Antonia et al., "Synergy of fosfomycin with other antibiotics for Gram-positive and Gram-negative bacteria," *Eur J Clin Pharmacol* 66:359-368, 2010.
Harada et al., "Urinary Pharmacokinetic and Pharmacodynamic Profiles of Fosfomycin Against Extended-Spectrum β-Lactamase-Producing *Escherichia coli* with Canine Ex Vivo Modeling: a Pilot Study," *Antibiotics* 9:1-7, 2020.
Lerk et al., "Effect of Microscrystalline Cellulose on Liquid Penetration in and Disintegration of Directly Compressed Tablets," *J Pharm Scil.* 68(2):205-211, Feb. 1979.
Pérez et al., "Fosfomycin: Uses and potentialities in veterinary medicine," *Open Veterinary Journal* 4(1): 26-43, 2014.
Falagas et al., "Fosfomycin," *Clin Microbiol Rev* 29:321-347, Mar. 9, 2016.
Rudenko et al., "Prevention of Recurrent Lower Urinary Tract Infections by Long-term Administration of Fosfomycin Trometamol," *Arzneim.-Forsch./Drug Res.* 55(7):420-427, 2005.

*Primary Examiner* — Kristin A Vajda
(74) *Attorney, Agent, or Firm* — SEED INTELLECTUAL PROPERTY LAW GROUP LLP

(57) ABSTRACT

The present invention concerns tablet formulations of fosfomycin trometamol, methods of manufacturing and using thereof. More specifically, it relates to an oral pharmaceutical composition in tablet form comprising or consisting of:
a. fosfomycin trometamol;
b. a low moisture diluent selected from the group consisting of anhydrous calcium hydrogen phosphate, anhydrous microcrystalline cellulose and combinations thereof;
c. optionally, a lubricant; and
d. optionally, other pharmaceutically acceptable excipients.

19 Claims, 12 Drawing Sheets

| Injection Order No | 1 | | | | | | |
|---|---|---|---|---|---|---|---|
| Sample Name | | Type | Injection Order No | Name | RT [min] | Area | % Area |
| GAL-2910-01 DT1 | | MM m | 1 | Impureza B | 4.200 | 1000.13 | 0.05 |
| GAL-2910-01 DT1 | | MM m | 1 | Impureza A | 7.256 | 16653.24 | 0.86 |
| GAL-2910-01 DT1 | | MM m | 1 | Fosfomicina | 8.027 | 1909200.60 | 99.08 |

Fig. 2a

| Injection Order No | 1 | | | | | | |
|---|---|---|---|---|---|---|---|
| Sample Name | | Type | Injection Order No | Name | RT [min] | Area | % Area |
| GAL-2910-02 DT1 | | MM m | 1 | Impureza B | 4.199 | 1184.70 | 0.06 |
| GAL-2910-02 DT1 | | MM m | 1 | Impureza A | 7.228 | 15717.51 | 0.82 |
| GAL-2910-02 DT1 | | MM m | 1 | Fosfomicina | 7.979 | 1896092.79 | 99.12 |

Fig. 3a

Injection Order No   1

| Sample Name | Type | Injection Order No | Name | RT [min] | Area | % Area |
|---|---|---|---|---|---|---|
| GAL-2910-03 DT1 | MM m | 1 | Impureza B | 4.191 | 994.74 | 0.05 |
| GAL-2910-03 DT1 | MM m | 1 | Impureza A | 7.198 | 806.47 | 0.04 |
| GAL-2910-03 DT1 | MM m | 1 | Fosfomicina | 7.900 | 1962885.78 | 99.91 |

Fig. 4a

| Injection Order No | 1 | | | | | |
|---|---|---|---|---|---|---|
| Sample Name | Type | Injection Order No | Name | RT [min] | Area | % Area |
| GAL-2910-04 DT1 | MM m | 1 | Impureza B | 4.193 | 1084.85 | 0.06 |
| GAL-2910-04 DT1 | MM m | 1 | Impureza A | 7.172 | 15482.04 | 0.80 |
| GAL-2910-04 DT1 | MM m | 1 | Fosfomicina | 7.893 | 1908919.63 | 99.14 |

Fig. 5a

| Injection Order No | 1 | | | | | | |
|---|---|---|---|---|---|---|---|
| Sample Name | | Type | Injection Order No | Name | RT [min] | Area | % Area |
| GAL-2910-05 DT1 | | MM m | 1 | Impureza B | 4.201 | 1672.58 | 0.09 |
| GAL-2910-05 DT1 | | MM m | 1 | Impureza A | 7.143 | 11713.50 | 0.61 |
| GAL-2910-05 DT1 | | MM m | 1 | Fosfomicina | 7.856 | 1918029.93 | 99.31 |

Fig. 6a

FOSFOMYCIN TABLET FORMULATIONS

FIELD OF THE INVENTION

The present invention concerns tablet formulations of fosfomycin trometamol, methods of manufacturing and using thereof. In particular, it relates to fosfomycin trometamol tablets intended for veterinary use, more specifically for companion animals, such as cats and dogs.

BACKGROUND OF THE INVENTION

Fosfomycin is a broad-spectrum antibiotic produced by certain *Streptomyces* species which is typically used in humans in the treatment of urinary tract infections in a single oral dose of fosfomycin trometamol (3 g of fosfomycin base) formulated as a granulate (Monurol®). Other powder granulate fosfomycin trometamol formulations are described in EP 1 747 781 B1, EP 2 656 846 B1 or ES 2 224 869 B1.

The potential use of fosfomycin in domestic animal medicine has previously been described (Perez et al., Open veterinary Journal 2014, 4(1):26-43). It is known that fosfomycin tends to form salts easily due to its acidic nature and it has been used in the form of different salts: disodium salt is typically used for intravenous and subcutaneous administration, while trometamol salt (tromethamine [trihydroxymethyl aminomethane]) and the calcium salt are used for oral administration. From the disclosure at Perez et al., 2014 (i.e., see Table 3), it appears that fosfomycin trometamol has not previously been used in animals.

Fosfomycin trometamol is the fosfomycin salt with a higher absorption rate. Nevertheless, it presents high hygroscopicity and poor stability in water and thus cannot be formulated as a solution.

This problem may be overcome by formulating fosfomycin trometamol as a solid form. As discussed above, fosfomycin trometamol granulate formulations have already been described for human use. However, granulate dosage form is not preferred for veterinary use, in particular for company animals (i.e., cats and dogs), since the dose will oftentimes have to be adapted according to the weight of the animal. In order to solve this problem, typically pets' medicines are formulated as tablets with a break mark.

Formulating fosfomycin trometamol tablets has been challenging due to the high doses of active ingredient recommended. Accordingly, to avoid a final product which has a total weight which is too high, and thus which may difficult palatability and compliance, when formulating fosfomycin trometamol tablets, it will be required to reduce the amount of excipients as much as possible while preserving good pharmacotechnical properties.

IT 1348011 B1 describes tablets or microtablets consisting of 97-100% by weight of fosfomycin trometamol and 0-3% of a lubricant. These formulations are disclosed for direct compression in dosages of 3 g of fosfomycin base (5,631 g fosfomycin trometamol) or tablets with 50% of this dose. Accordingly, the powder mixture for direct compression described therein has no excipient other than a lubricant. This document provides no experimental data whatsoever, thus it does not make plausible that such formulations provide fosfomycin trometamol tablets with suitable pharmacotechnical, stability or palatability properties. A person skilled in the art would expect that the size of a tablet with such a high weight (about 6 g), would be associated to palatability problems.

Therefore, the invention addresses the need to provide a stable formulation of fosfomycin trometamol in tablet form with suitable pharmacotechnical properties, thus providing a suitable pharmaceutical form for fosfomycin trometamol administration to companion animals, which enables to adapt the administered fosfomycin trometamol amount to the animal weight. Preferably, said tablet would further present good palatability properties.

SUMMARY OF THE INVENTION

It has surprisingly been found that the combined use of anhydrous calcium hydrogen phosphate and anhydrous microcrystalline cellulose as diluents in the fosfomycin trometamol formulation enabled to obtain a particulate mixture which had superior flow and compressibility properties with respect to other anhydrous diluents for direct compression commonly used in the art as shown in Example 1.1. A powder mixture having good flow properties avoids segregation events and/or cavern formation thus resulting in appropriate active ingredient distribution and tablet weight and dose uniformity.

In addition, a fosfomycin trometamol tablet comprising anhydrous calcium hydrogen phosphate and anhydrous microcrystalline cellulose was found to have superior chemical stability properties in acidic media with respect to compositions in the absence of any diluents or using other anhydrous diluents, as shown in Example 1.2.

Accordingly, the first aspect of the invention relates to an oral pharmaceutical composition in tablet form comprising or consisting of:
  a. fosfomycin trometamol;
  b. a low moisture diluent selected from the group consisting of anhydrous calcium hydrogen phosphate, anhydrous microcrystalline cellulose and combinations thereof;
  c. optionally, a lubricant; and
  d. optionally, other pharmaceutically acceptable excipients.

In a second aspect of the invention, a method of manufacturing an oral fosfomycin trometamol tablet composition as described herein comprises or consists of the steps of:
  i. mixing a diluent selected from the group consisting of anhydrous calcium hydrogen phosphate, anhydrous microcrystalline cellulose and combinations thereof with fosfomycin trometamol, and optionally a further pharmaceutically excipient; and
  ii. optionally, mixing a lubricant with the blend obtained in i);
  iii. pressing the blend obtained in ii) with a tablet press machine and thereby obtaining the tablets.

In a third aspect, the invention refers to an oral fosfomycin trometamol tablet composition as described herein, for use as a medicament.

In fourth aspect, the invention refers to an oral fosfomycin trometamol tablet composition as described herein, for use in a method of prophylactically or therapeutically treating an infection in a subject.

In a related aspect, provides a method of prophylactically or therapeutically treating an infection comprising administering to a subject in need of such treatment a therapeutically effective amount of the oral fosfomycin trometamol tablet composition of the invention.

In an additional aspect, the present invention also provides a kit based on the compositions described in the present application. Such a kit is particularly suitable for use in the medical methods described herein.

BRIEF DESCRIPTION OF THE DRAWINGS

FIG. 2a. Forced Degradation Study_Acid Conditions Formulation D1.1: results table.

FIG. 3a. Forced Degradation Study_Acid Conditions Formulation D1.2: results table.

FIG. 4a. Forced Degradation Study_Acid Conditions Formulation L3: results table.

FIG. 5a. Forced Degradation Study_Acid Conditions Formulation L4: results table.

FIG. 6a. Forced Degradation Study_Acid Conditions Formulation L5: results table.

DETAILED DESCRIPTION OF THE INVENTION

Definitions

Figure 1:
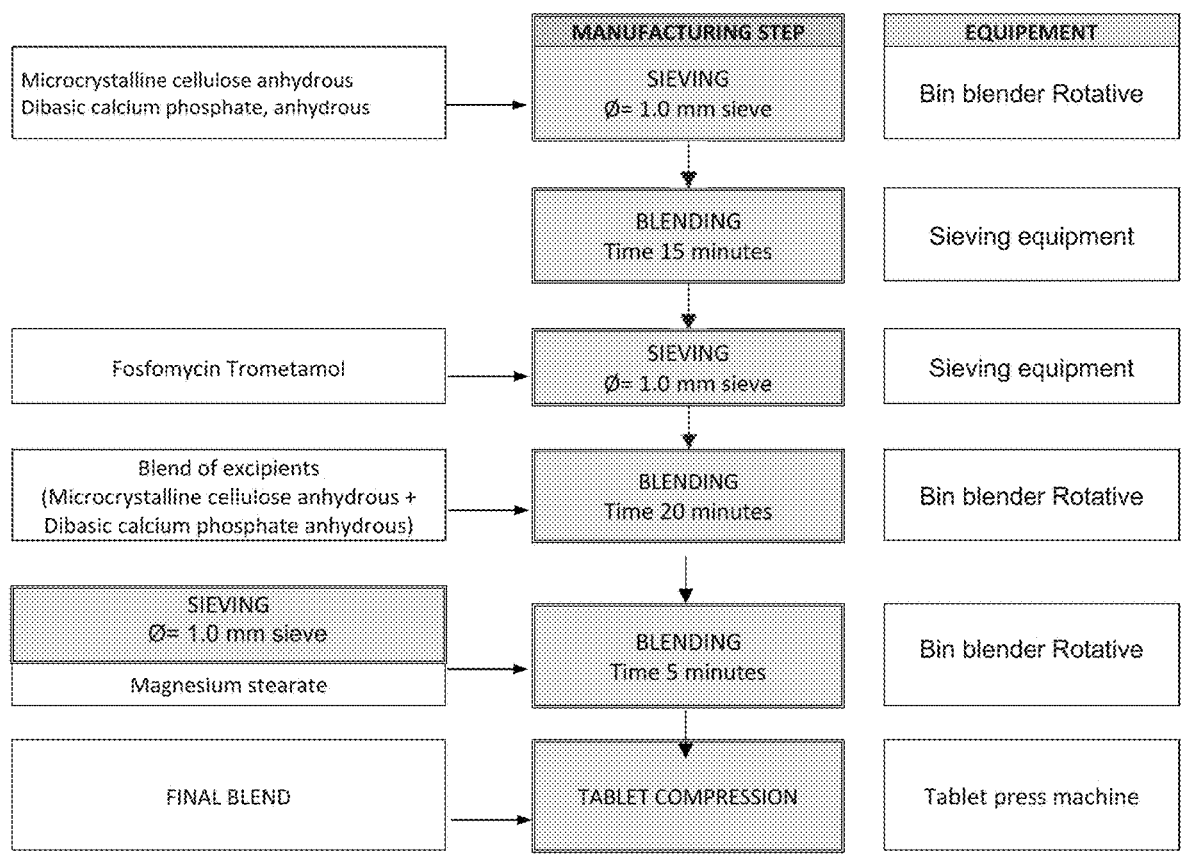
FIG. 1. Workflow generally illustrating the direct compression manufacturing process.
Figure 2B:
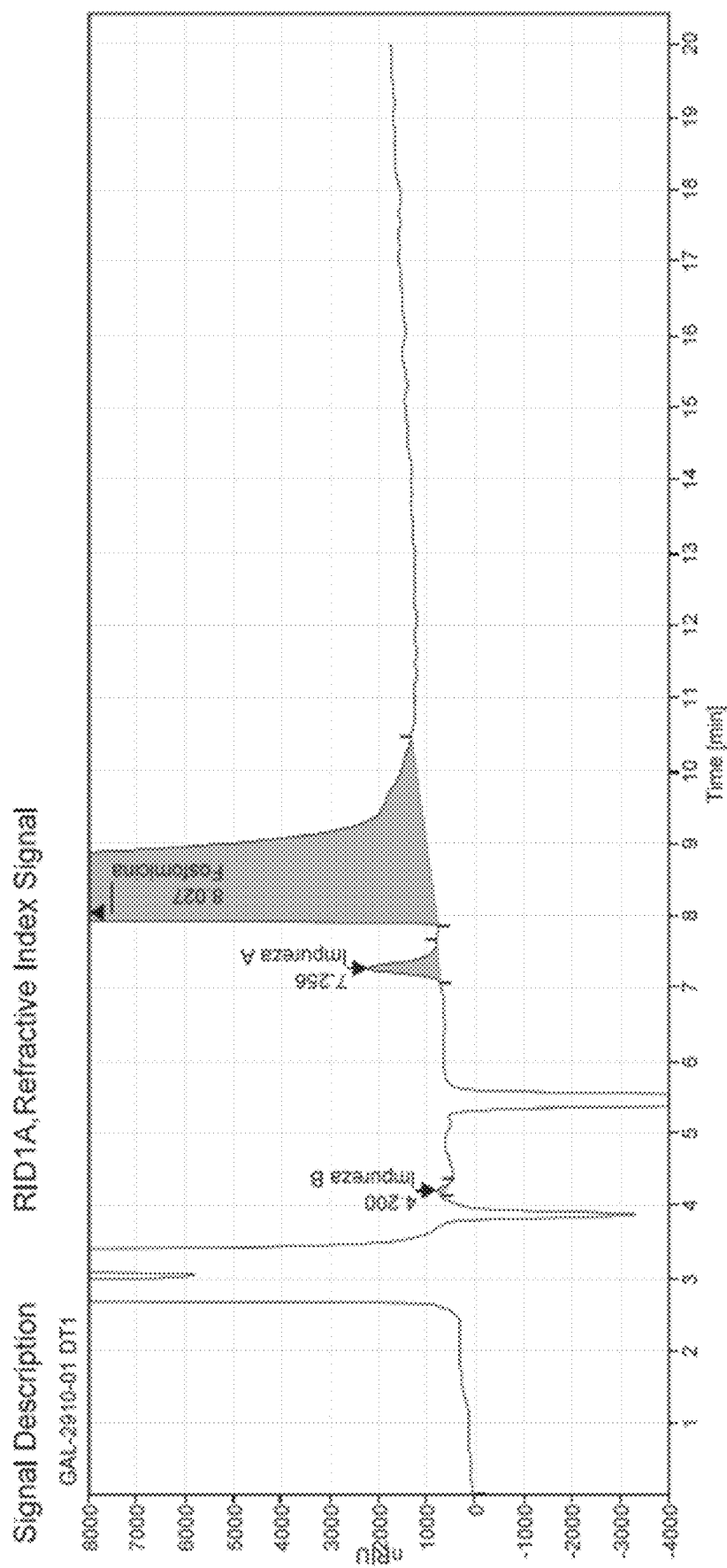
FIG. 2b. Forced Degradation Study_Acid Conditions Formulation D1.1: chromatogram.
Figure 3B:
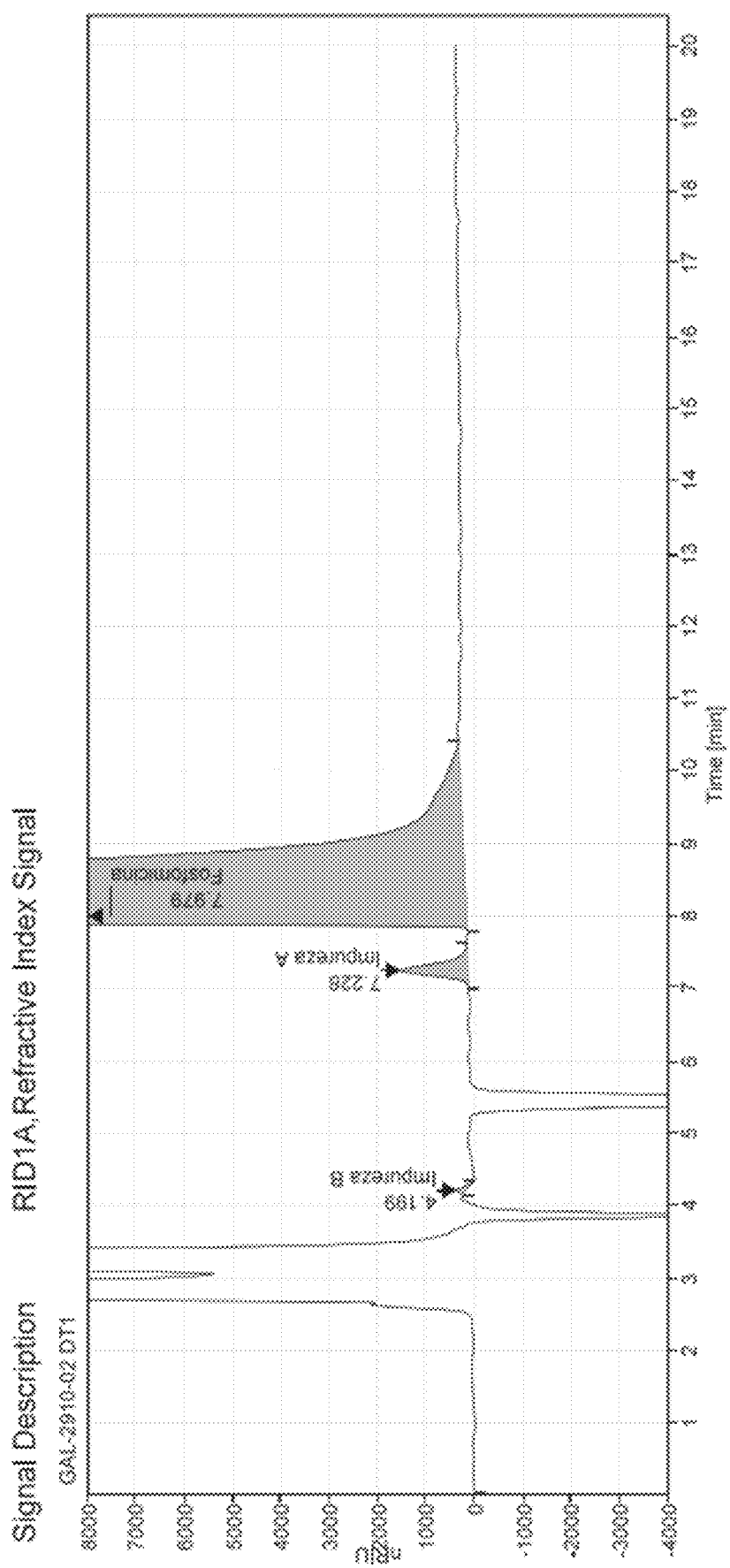
FIG. 3b. Forced Degradation Study_Acid Conditions Formulation D1.2: chromatogram.
Figure 4B:
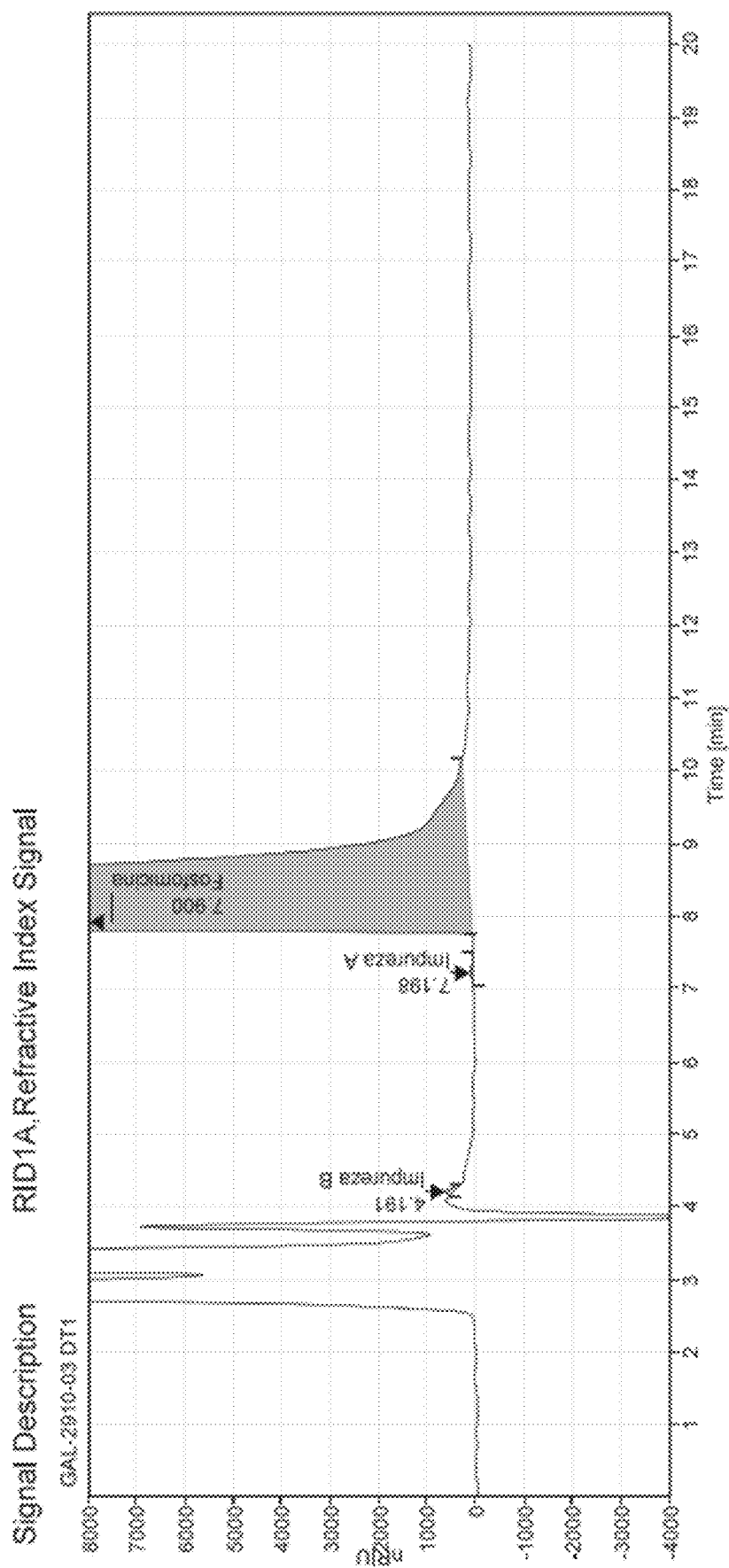
FIG. 4b. Forced Degradation Study_Acid Conditions Formulation L3: chromatogram.
Figure 5B:
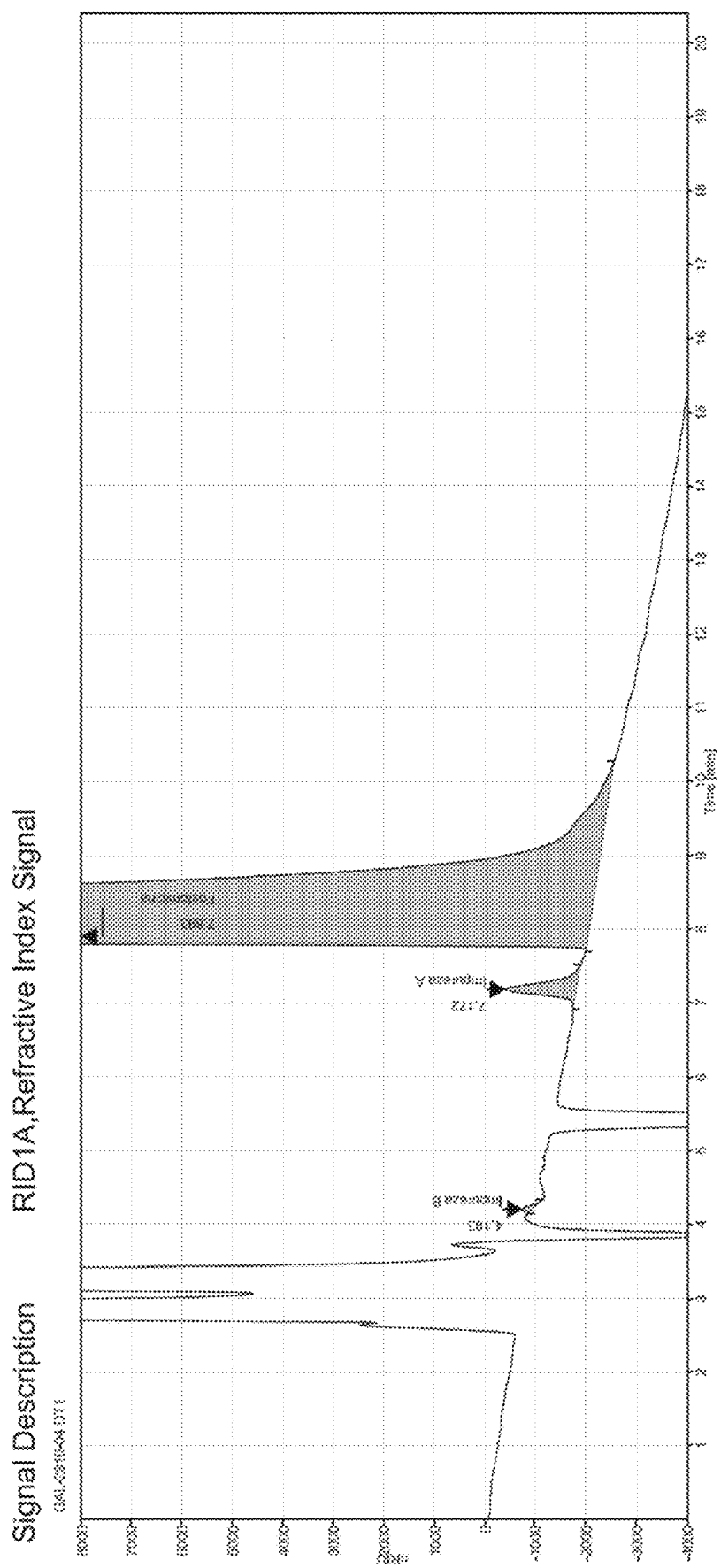
FIG. 5b. Forced Degradation Study_Acid Conditions Formulation L4: chromatogram.
Figure 6B:
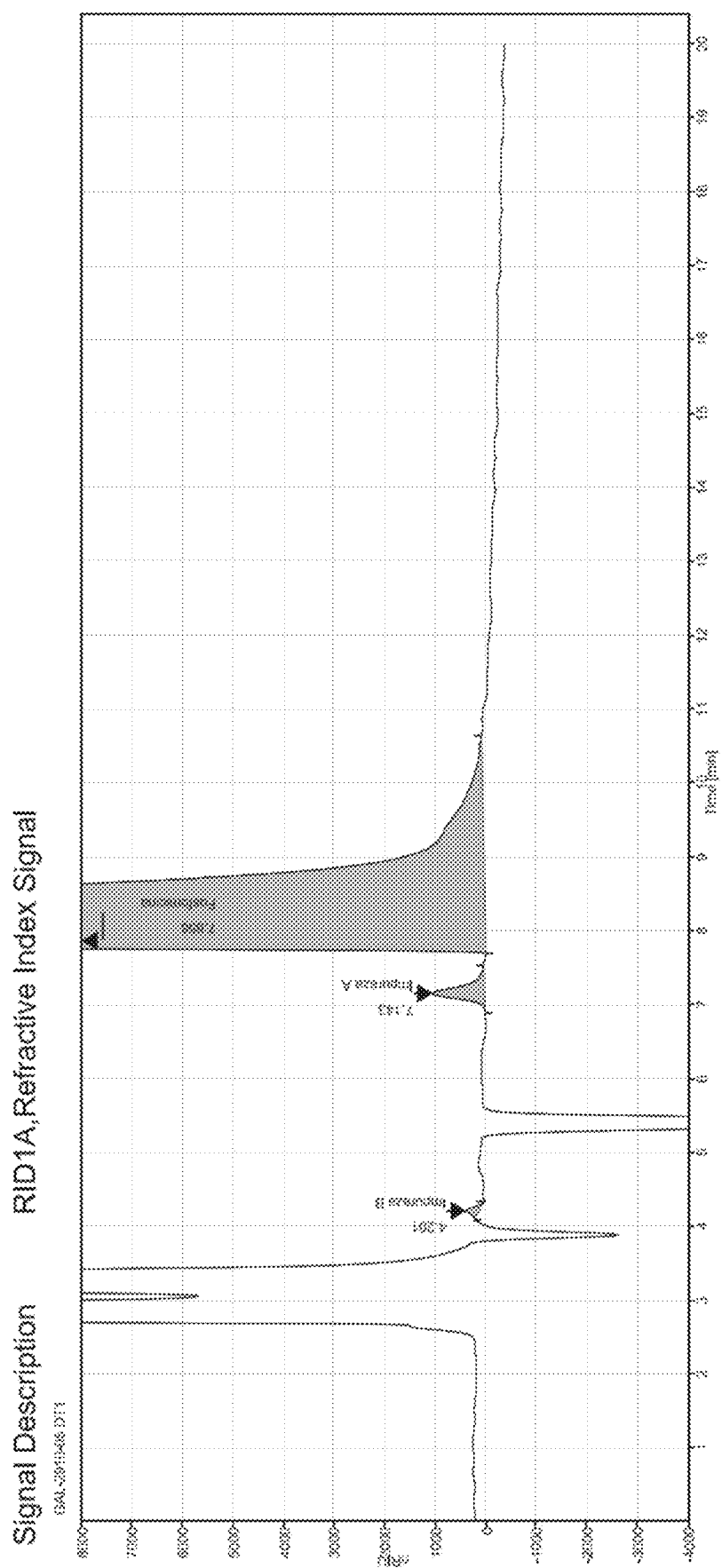
FIG. 6b. Forced Degradation Study_Acid Conditions Formulation L5: chromatogram.

The term "pharmaceutically acceptable" as used herein refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The term "excipient" or "pharmaceutically acceptable excipient" as used herein refers to carriers, excipients, or vehicles such as those described herein and in Remington's Pharmaceutical Sciences 22th edition (2013).

The terms "subject", or "individual'" are used herein interchangeably to refer to all the animals classified as mammals and includes but is not limited to domestic and farm animals, primates and humans, for example, human beings, non-human primates, cows, horses, pigs, poultry, sheep, goats, dogs, cats, or rodents. In preferred embodiments, said subject is a human. In other preferred embodiments, said subject is a companion animal, such as cats and dogs.

The term "treatment" encompasses both a prophylactic and therapeutic treatment. The term "therapeutic treatment" or "therapy" as used herein refers to bringing a body from a pathological state or disease back to its normal, healthy state. The term "prophylactic treatment" as used herein refers to preventing a pathological state. This treatment may be a combined treatment or therapy. Treatment also refers to reducing incidence, or alleviating symptoms, eliminating recurrence, preventing recurrence, preventing incidence, improving symptoms, improving prognosis or combinations thereof. "Treatment" further encompasses reducing the population, growth rate or virulence of the bacteria in the subject and thereby controlling or reducing a bacterial infection in a subject or bacterial contamination of an organ or tissue or environment. On the other hand, "treatment" of an already established infection refers to reducing the population or killing, including even eradicating the Gram-positive or Gram-negative bacteria responsible for an infection.

As used herein a "therapeutically effective amount" refers to an amount effective, at dosages and for periods of time necessary to achieve the desired therapeutic result, such as one or more of the following therapeutic results, such as a significant delay of the onset or progression of the disease; or a significant reduction of the severity of one or more symptoms. A therapeutically effective amount is also typically one in which any toxic or detrimental effect of the active ingredient or pharmaceutical composition is outweighed by the therapeutically beneficial effects.

The term "combination therapy" as used throughout the specification, is meant to comprise the administration of the referred therapeutic agents to a subject, in the same or separate pharmaceutical formulations, and at the same time or at different times. If the therapeutic agents are administered at different times they should be administered sufficiently close in time to provide for the combined effect (e.g. potentiating or synergistic response) to occur. The particular combination of therapies to employ in a combination regimen will take into account compatibility of the desired therapeutics and/or procedures and/or the desired therapeutic effect to be achieved. It will be appreciated that the therapies employed may achieve a desired effect for the same disorder, and/or they may achieve different effects (e.g., control of any adverse effects).

DETAILED DESCRIPTION OF THE INVENTION

In a first aspect, the present invention relates to an oral pharmaceutical composition in tablet form comprising or consisting of:
a. fosfomycin trometamol;
b. a low moisture diluent selected from the group consisting of anhydrous calcium hydrogen phosphate, anhydrous microcrystalline cellulose and combinations thereof;
c. optionally, a lubricant; and
d. optionally, other pharmaceutically acceptable excipients.

Fosfomycin trometamol, which chemical name is mono (2-ammonium-2-hydroxymethyl-1,3-propanedi-ol) (2R, cis)-(3-methyloxiranyl)phosphonate, is an antibiotic indicated in the prophylaxis and treatment of uncomplicated acute infections of the lower urinary tract, in particular in woman and adolescent girls. Fosfomycin trometamol can be found in amorphous or crystalline form, preferably on crystalline form.

Fosfomycin trometamol can represent from 70%, 75% or 80% to 95% w/w of the composition, preferably from 80% to 90% w/w, more preferably about 85% w/w. In some embodiments, the content of fosfomycin base is of at least 250 mg, preferably of at least 500 mg, more preferably of at least 750 mg, even more preferably of at least 1000 mg, 1100 mg, 1200 mg, 1300 mg, 1400 mg, 1500 mg, 1600 mg, 1700 mg, 1800 mg, 1900 mg or higher. In preferred embodiments, the content of fosfomycin base is from 500 mg to 1500 mg. For instance, formulations of 500 mg, 1000 mg or 1500 mg of fosfomycin base, corresponding to 0.94 g, 1.88 g and 2.82 g of fosfomycin trometamol respectively.

In some embodiments, fosfomycin trometamol is in the form of a powder consisting of particles having a mean diameter (d50) of about 60 µm to about 550 µm, preferably of about 100 µm to about 200 µm, more preferably about 170 µm when particle size distribution of fosfomycin trometamol is determined using laser diffraction (wet method).

The term "anhydrous" as used herein means that the excipient has a humidity content of less than 2% w/w. Preferably, said anhydrous diluent as defined herein above, is characterized by having a humidity content of less than 1.5% w/w, preferably of less than 1% w/w, more preferably of less than 0.5% w/w, less than 0.4% w/w, less than 0.3% w/w, less than 0.2% w/w, even more preferably less than 0.1% w/w. For instance, water content can be determined according to USP <921> water determination method Ia (e.g. USP 42 <921> water determination method), for instance by Karl Fisher Volumetric Titration using Mettler Toledo V30 Karl Fisher Titrator.

Said diluent may be found at an amount from 5% to 20% w/w of the composition, preferably from 10% to 20% w/w, more preferably from 13% to 17% w/w, even more preferably from 14% to 15% w/w.

Anhydrous calcium hydrogen phosphate and anhydrous microcrystalline cellulose (mcc) can be found at different relative proportions. For instance, these can be found at 5:1, 4:1, 3:1, 2:1, 1:1, 1:2, 1:3, 1:4 or 1:5 ratios. In preferred embodiments, anhydrous calcium hydrogen phosphate and microcrystalline cellulose are found at a 2:1 to 1:2 ratio, preferably at a 1:1 ratio.

Microcrystalline cellulose (mcc) may be in the form of a powder consisting of particles having a mean diameter (d50) of about 20 µm to about 250 µm, preferably of about 130 µm to about 230 µm, more preferably of about 170 µm when particle size distribution is determined using laser diffraction (wet method). Examples of anhydrous mcc which can be used in the composition of the invention are VIVAPUR® 103, 112, 14 AND 200 XLM.

Calcium hydrogen phosphate may be in the form of a powder consisting of particles having a mean diameter (d50) of about 60 µm to about 550 µm, preferably of about 120 µm to about 240 µm, more preferably (d50) of about 200 µm when particle size distribution is determined using laser diffraction (wet method).

In some embodiments, said composition can contain other anhydrous diluents, with the exception of sugars. For instance, it may contain colloidal silicon dioxide (CSD). In preferred embodiments, the composition comprises anhydrous calcium hydrogen phosphate and anhydrous microcrystalline cellulose as only diluents.

Suitable "lubricants", may be for instance, stearic acid; stearic acid metal salts such as calcium stearate or magnesium stearate; sucrose stearate, talc; colloidal silica; waxes such as beeswax or spermaceti; boric acid; adipic acid; sulfates such as sodium sulfate; glycol; fumaric acid; sodium stearyl fumarate; sucrose fatty acid esters; sodium benzoate; D,L-leucine; lauryl sulfates such as sodium lauryl sulfate or magnesium lauryl sulfate; silicates such as silicic anhydride or hydrated silicate; or the aforementioned starch derivatives. Of these, stearic acid or stearic acid metal salts are preferably used. In preferred embodiments, said lubricant is magnesium stearate.

The lubricant can be found at an amount from 0.1% to 5% w/w of the composition, preferably from 0.1% to 3% w/w, more preferably from 1.5% to 2.5% w/w, even more preferably about 2% w/w.

The fosfomycin trometamol composition as described herein can also comprise, as in normal practice, additional substances other than inert diluents and a lubricant, such as surface-active agents and/or emulsifiers, granulating and/or disintegrating agents, binding agents, preservatives, buffering agents, sweetener and/or flavouring agents.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Flavouring agents are normally used to improve palatability. In particular embodiments, the tablets as described herein comprise flavouring agents generally used to increase pet's food palatability, such as chicken flavour, beef flavour, fish flavour, orange flavour or mandarin flavour. In preferred embodiments, said flavour is beef flavour (e.g., Beef flavour Aroma PC 0125, Pet Flavors Inc.).

In some embodiments, said other pharmaceutical excipient consist of a flavouring agent. In other embodiments, the oral composition does not comprise other pharmaceutical excipients.

In further some embodiments, this oral composition comprises or consists of:
 a. from 80% to 95% w/w of fosfomycin trometamol;
 b. from 5% to 20% w/w of a diluent with a humidity content of less than 1.5%, selected from the group consisting of anhydrous calcium hydrogen phosphate, anhydrous microcrystalline cellulose and combinations thereof;
 c. optionally, from 0.1% to 3% w/w of a lubricant; and
 d. optionally, other pharmaceutically acceptable excipients in quantity enough to complete the 100% of the composition total weight.

In some embodiments thereof, said composition comprises from 2% to 10% w/w of anhydrous calcium hydrogen phosphate and 2% to 10% w/w of anhydrous microcrystalline cellulose.

In preferred embodiments thereof, said composition comprises from 5% to 10% w/w of anhydrous calcium hydrogen phosphate and 5% to 10% w/w of anhydrous microcrystalline cellulose.

Preferred amounts of each of these components are as defined herein above. In a preferred embodiment, this oral composition comprises or consists of:
 a. from 80 to 85% w/w of fosfomycin trometamol, preferably about 85% w/w;
 b. from 5% to 10% w/w of microcrystalline cellulose anhydrous, preferably about 7% w/w;
 c. from 5% to 10% w/w of dibasic calcium phosphate anhydrous, preferably about 7% w/w; and
 d. from 1.5% to 2.5% w/w of magnesium stearate; preferably about 2% w/w; and
 e. from 0% to 10% w/w a flavoring agent, preferably about 5% w/w.

In another preferred embodiment, this oral composition comprises or consists of:
 a. from 80 to 90% w/w of fosfomycin trometamol, preferably about 85% w/w;
 b. from 2% to 10% w/w of microcrystalline cellulose anhydrous, preferably about 7% w/w;
 c. from 2% to 10% w/w of dibasic calcium phosphate anhydrous, preferably about 7% w/w; and
 d. from 1.5% to 2.5% w/w of magnesium stearate; preferably about 2% w/w; and
 e. from 0% to 10% w/w a flavoring agent, preferably about 5% w/w.

In some embodiments, this tablet can or not be a film-coated tablet. This coating can be a modified-release or gastro-resistant coating. In preferred embodiments, the tablet as described herein does not comprise a modified-release or gastro-resistant coating.

Conventional materials used for film coating are well known in the art and described for instance in Pharmaceutical Coating Technology (G. Cole (ed.), 1995). Film coating formulations usually contain the following components: polymer(s), plasticizer(s), colourant(s)/opacifier(s), and diluents/vehicle(s). In addition, minor quantities of flavours, surfactants and waxes may also be used.

The majority of the "polymers" used in film coating are either cellulose derivatives, such as cellulose ethers, such as hydroxyethylcellulose, hydroxypropylcellulose, hydroxypropylmethylcellulose (hypromellose) and methylcellulose, or acrylic polymers and copolymers. Occasionally encountered are high molecular weight polyethylene glycols, polyvinyl pyrrolidone, polyvinyl alcohol and waxy materials. Their function usually is to prevent bad mouth feel and/or taste and in some cases degradation, e.g. oxidation of the active ingredients and/or pharmaceutical additives used.

Commonly used "plasticizers" can be categorized into three groups:
polyols such as glycerol, propylene glycol and macrogols,
organic esters such as phthalate esters, dibutyl sebacetate, citrate esters and triacetin,
oils/glycerides such as castor oil, acetylated monoglycerides and fractionated coconut oil.

The coloring agent/opacifier may be for instance water insoluble pigments such as titanium oxide, iron oxide, iron sesquioxide, yellow iron sesquioxide or water-soluble colourants.

The total weight of the tablet will vary according to the desired administration dosage. In some embodiments, the tablets described herein have a total weight from about 500 mg to about 3500 mg, such as 500 mg, 1000 mg, 1500 mg, 2000 mg, 2500 mg or 3000 mg. In some embodiments, the tablets described herein have a total weight from about 1000 mg to about 3500 mg.

For instance, a tablet of the formulation L3 described in the Examples, would have a total weight of 1.12 g, 2.22 g and 3.34 g for a fosfomycin base content of 0.5 g, 1 g and 1.5 g, respectively. Thus, in preferred embodiments, tablets with a FOS base content of 0.5 g have a total weight of from 1 g to 1.25 g, of 1 g FOS base have a total weight of from 2 to 2.5 g and of 1.5 g FOS base have a total weight of from 3 to 3.5 g.

The hardness of the tablet may be any hardness that allows for tablet formation and its subsequent disaggregation in the stomach. In a particular embodiment, the tablet of the invention has a hardness of about 40 N to 300N, preferably about 50 N to about 200 N. For instance, tablets of 0.5 g of fosfomycin base may have a tablet hardness of 40 N to and 150 N, tablets of 1 g of fosfomycin base may have a tablet hardness of 45 N to 250 N and tablets of 1.5 g of fosfomycin base may have a tablet hardness of 200 N to 270 N.

In some embodiments, the fosfomycin trometamol tablets of the invention are characterized by having a dosage uniformity complying with the European Pharmacopeia standards.

The term "dosage uniformity" as used herein refers to the degree of uniformity in the amount of the active substance among dosage units; defining dosage units as dosage forms containing a single dose or a part of a dose of the active substance in each dosage unit. To ensure the dosage uniformity, each dosage unit should have an active substance content within a narrow range around the label claim. The dosage uniformity of the pharmaceutical compositions according to the present invention can be measured by means of performing the test for content uniformity, as states in European Pharmacopeia (2.9.40, monograph). As defined therein, the requirements for dosage uniformity are met if the acceptance value of the dosage units is less than or equal to 15. The acceptance value (AV) is a figure which characterized the dosage uniformity. The acceptance value is calculated, as stated in the European Pharmacopeia 7.0. (2.9.40, monograph).

In other embodiments, the tablets described herein are characterized by having chemical stability. As described in Example 1.2, the tablets of the invention have shown stability of fosfomycin trometamol under forced acid, basic and oxidative conditions conducted at room temperature (20-25° C.). They further showed chemical stability at different temperatures.

Chemical stability of the active ingredient may be determined by measuring the percentage of known degradation products (e.g. by HPLC as described at *Fosfomycin Trometamol* January/2017:1425 *European Pharmacopoeia monograph*) after submitting the composition to forced degradation conditions.

As shown in Example 1.2, it is particularly striking the stabilizing effect of the diluent excipients used in the claimed fosfomycin trometamol composition under forced acidic conditions. In particular, it is shown that in formulations where no diluent was used or wherein other anhydrous diluents were used there was an extraordinary increase in the percentage of impurity A. In particular, formulations D1.1 and D1.2 described in IT 1348011 B1 presented an increase of impurity A of 4.5 fold and 6.8 fold respectively, whereas for formulation L3 of the invention the levels of impurity A in the initial conditions were maintained.

According to the *Fosfomycin Trometamol* January/2017: 1425 *European Pharmacopoeia monograph* the following levels of impurities are allowed at the end of the shelf-life of a FT pharmaceutical form:
Impurity A≤0.3%
Impurity B≤0.3%
Impurity C≤0.1%
Impurity D≤0.1%
Individual unknown impurity (max)≤0.10%
total impurities≤1.0%.

As shown in Example 1.2, for all formulations other than L3, the levels of impurity A were found to be superior to 0.3%. Accordingly, for all the other tested formulations, the levels of impurity A were significantly superior to the established limit for the shelf-life specification.

In preferred embodiments, the tablets of the invention are characterized by a very high stability of the active ingredient, in particular under forced acid conditions (e.g., under the conditions described in the Examples). In preferred embodiments, the pharmaceutical composition of the invention is characterized by comprising a content of impurity A of less than 0.3%, preferably less than 0.2%, preferably less than 0.1%, more preferably less than 0.09%, 0.08%, 0.07%, 0.06% or 0.05%, especially after being submitted to forced degradation under acid conditions.

Methods for the manufacturing of pharmaceutical tablets are well known in the art, such as wet granulation, dry granulation or direct compression. In wet granulation, components are typically mixed and granulated using a wet binder. The wet granulates are then sieved, dried and optionally ground prior to compressing into tablets. Dry granulation is usually described as a method of controlled crushing of precompacted powders densified by either slugging or passing the material between two counter-rotating rolls. More specifically, powdered components that may contain very fine particles are typically mixed prior to being compacted to yield hard slugs which are then ground and sieved before the addition of other ingredients and final compression to form tablets. Direct compression is generally considered to be the simplest and the most economical process for producing tablets. However, it may only be applied to materials that don't need to be granulated before tableting. Direct compression requires only two principal steps; i.e., the mixing of all the ingredients and the compression of this mixture. However, direct compression is applicable to only a relatively small number of substances as the ingredients of the tablets often need to be processed by some granulation technique to make them compressible and/or for improving their homogeneity and flowability.

In some embodiments, the oral tablet composition described herein has been obtained by direct compression. Direct compression is the tablet manufacturing process which requires a minimum number of steps. Nevertheless, it's suitability will depend on the properties of the active substance. In the present case, direct compression is preferred in view of the high hygroscopicity of fosfomycin. Direct compression is preferred for fosfomycin because the number of steps is less than in a granulation process, and it means less exposition to the humidity.

In preferred embodiments, the tablets of the invention have been obtained by a method as described herein below under the second aspect of the invention. These tablets can be tablets with a break mark, for instance dividing the tablet in two or four equal portions to easy its division in fragments with substantially the same amount of active ingredient.

In a second aspect of the invention, a method of manufacturing an oral fosfomycin trometamol tablet composition as described herein comprises or consists of the steps of:
i. mixing a diluent selected from the group consisting of anhydrous calcium hydrogen phosphate, anhydrous microcrystalline cellulose and combinations thereof with fosfomycin trometamol, and optionally a further pharmaceutically excipient; and
ii. optionally, mixing a lubricant with the blend obtained in i);
iii. pressing the blend obtained in ii) with a tablet press machine and thereby obtaining the tablets.

In some embodiments, when said diluent is anhydrous calcium hydrogen phosphate and anhydrous microcrystalline cellulose, the diluents can be mixed together prior to step i). Also, prior to each mixing state the ingredients will be typically sieved, for instance with a sieve having a diameter from 0.5 mm to 2.5 mm, preferably with a sieve having a diameter of 1 mm. In preferred embodiments, said method of manufacture is a direct compression method comprising the steps shown in FIG. 1.

Medical Uses of the Invention

In a third aspect, the invention refers to an oral fosfomycin trometamol tablet composition as described herein, for use as a medicament.

In fourth aspect, the invention refers to an oral fosfomycin trometamol tablet composition as described herein, for use in a method of prophylactically or therapeutically treating an infection in a subject. In a related aspect, provides a method of prophylactically or therapeutically treating an infection comprising administering to a subject in need of such treatment a therapeutically effective amount of the oral fosfomycin trometamol tablet composition of the invention.

The infection may be caused by Gram-positive and/or Gram-negative bacteria. Moreover, it may occur in any organ or tissue of the subject. In a particular embodiment, the infection may occur in blood, gastrointestinal tract, heart, cardiovascular system, liver, lung, respiratory tract, kidney, urinary tract, nervous central system, skin, subcutaneous tissues or surgical wounds.

In a more particular embodiment, the infection is a urinary infection. Fosfomycin is known to have good in vitro activity against common uropathogens, such as *Escherichia coli* (including extended-spectrum β-lactamase-producing *E. coli*), *Proteus mirabilis, Klebsiella pneumoniae* and *Staphylococcus saprophyticus*.

The effective quantity of the agent of the invention can vary within a wide range and, in general, will vary depending on the particular circumstances of application, duration of the exposure and other considerations. In a particular embodiment, the daily dose of fosfomycin base may range from 10 mg/kg to 70 mg/kg, preferably from 20 mg/kg to 60 mg/kg, such 25 mg/kg, 30 mg/kg, 35 mg/kg, 40 mg/kg, 45 mg/kg, 50 mg/kg or 55 mg/kg.

In some embodiments, said infection is an infection of the urinary tract. Fosfomycin trometamol is authorized in humans in the form of a daily administration of 3 g granules for oral suspension (fosfomycin trometamol) for the treatment of acute, uncomplicated cystitis in women and adolescent girls. Considering that a human adult has an average weight of about 50-60 kg, in a particular embodiment, said subject is a human adult and the daily administration is of 50-60 mg/kg.

In some embodiments, the subject to be treated is a companion animal, such as a cat or a dog. Cats have typically a weight from 3 kg to 7 kg, such as about 5 kg. Besides, dogs average weight will depend on their race. Dog can be classified depending on its race as belonging to small races (1.5 kg-13 kg), medium races (8 kg-40 kg) or large races (16 kg-90 kg). In some instances, the average weight of dogs can be considered to be about 20 kg.

In some embodiments, the dose of fosfomycin base for cats and dogs ranges from 30 mg/kg to 70 mg/kg. In a particular embodiment, the tablets of the invention have been devised to provide a dose of about 50 mg FOS base/kg in cats and about 70 mg FOS base/kg in dogs. Accordingly, in some embodiments, the fosfomycin trometamol tablets described herein have 250 mg (50 mg×5 kg) of FOS base (469.2 mg of fosfomycin trometamol), such tablets may be suitable for administration to cats or small dogs. In other embodiments, the fosfomycin trometamol tablets described herein have 1400 mg (70 mg×20 kg) of FOS base (2627.6 fosfomycin trometamol), such tablets may be suitable for administration to medium or large dogs.

One of the advantages of the fosfomycin trometamol tablets of the present invention, which may preferably contain a break mark, is that it enables the personalization of the fosfomycin trometamol treatment according to the weight of the companion animal. Accordingly, in some embodiments 1.5, 2, 2.5, 3, 3.5, 4, 4.5, 5, 5.5 or 6 daily pills can be administered to achieve the prescribed daily fosfomycin dosage.

For instance, in adult humans a daily dose of 3 g of fosfomycin base for oral administration can be administered as 2 tablets of 1.5 g, 3 tablets of 1 g or 6 tablets of 0.5 mg. For human children, the authorised daily dose is of 2 mg of fosfomycin base, which may be administered as 4 tablets of 0.5 g or 2 tablets of 1 g.

In some embodiments, the fosfomycin trometamol tablets described herein can be administered in combination with other drugs, such as other antibiotics. Examples of antibiotics that can be used with the fosfomycin trometamol tablets described herein include, without limitation, aminoglycoside antibiotics, ansamycins, carbacefem, carbapenems, cephalosporins, glycopeptides, macrolides, monobactams, penicillins, polypeptides, quinolones, sulfonamides, tetracyclines and others such as arsphenamine, chloramphenicol, clindamycin, lincomycin, ethambutol, fosfomycin, fusidic acid, furazolidone, isoniazid, oxazolidinones (e.g., linezolid), metronidazole, mupirocin, nitrofurantoin, platensimycin, pyrazinamide, quinupristin/dalfopristin, rifampin or rifampicin, tinidazole, viomycin and capreomycin; preferably cephalosporins, tetracyclines, glycopeptides, carbapenems, polypeptides, rifampicin, aminoglycosides, sulfonamides, viomycin and capreomycin.

Preferred combinations of fosfomycin trometamol with other antibiotics are those described to present synergistic activity against Gram-positive and/or Gram-negative bacteria (Antonia C. et al., European Journal of Clinical Pharmacology, Springer Verlag, 2010, 66 (4), pp. 359-368) For instance, the ability of fosfomycin to modify the production of penicillin-binding proteins (PBPs) enables its use for the treatment of MRSA infections as well as infections from penicillin-resistant *S. pneumoniae*. The ability of fosfomycin to penetrate biofilm layers encourages the use of fosfomycin in combination with other antibiotics against microbial strains growing on biofilms. Specifically, relevant studies report a synergistic effect of fosfomycin with quinolone antibiotic agents such as ulifloxacin, levofloxacin, and ofloxacin against *P. aeruginosa* biofilm isolates. Notably, fosfomycin is synergistic with N-acetylocysteine against *E. coli* biofilm isolates. Another aspect of fosfomycin that could prove useful, when it is used in combination with other antibiotic agents, is its ability to modify the toxicity of many types of co-administered drugs. Specifically, fosfomycin is reported to mitigate in vivo the toxicity of aminoglycosides, glycopeptides, as well as polymyxin B. Finally, it has been reported that the synergistic combination with either amoxicillin or clarithromycin may provide a useful alternative treatment option for patients with *Helicobacter pylori* infections.

In preferred embodiments, fosfomycin is the only active ingredient in the tablet composition.

Kit of the Invention

In an additional aspect, the present invention also provides a kit based on the compositions described in the present application. Such a kit is particularly suitable for use in the medical methods described above.

Said kit comprises one or more packaging units. One or more packaging units includes, without being limited to, 1, 2, 3, 4, 5 or 6 packaging units.

In some embodiments, each packaging unit of the kit comprises appropriate number of dosage units, such as 7, 14, 21 or 28 dosage units comprising an effective amount of the composition as described herein.

The packaging unit as described above may have one of the conventional forms usually used for oral pharmaceutical tablets. For example, the packaging unit may be a conventional blister pack comprising the appropriate number of dosage units in a sealed blister pack (e.g. an aluminium blister) with a cardboard, paperboard, foil or plastic backing and enclosed in a suitable cover. Each blister container may be conveniently numbered or marked in order to facilitate compliance.

The kit of the invention may comprise other appropriate components such as instructions for use.

Preferred embodiments and features of the kit are as described herein above for the oral composition and therapeutic methods and uses.

It is contemplated that any features described herein can optionally be combined with any of the embodiments of any medical use, pharmaceutical composition, kit, method of treatment, method of manufacturing a medicament of the invention; and any embodiment discussed in this specification can be implemented with respect to any of these. It will be understood that particular embodiments described herein are shown by way of illustration and not as limitations of the invention.

All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "comprises" also encompasses and expressly discloses the terms "consists of" and "consists essentially of". As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by ±1, 2, 3, 4, 5, 6, 7, 8, 9, or 10%. Accordingly, the term "about" may mean the indicated value±5% of its value, preferably the indicated value±2% of its value, most preferably the term "about" means exactly the indicated value (±0%).

The following examples serve to illustrate the present invention and should not be construed as limiting the scope thereof.

EXAMPLES

Example 1.—Fosfomycin Trometamol Tablets Formulation—Comparative Example

In the present example the inventors characterized the fosfomycin trometamol formulations' powder mixture and the tablets obtained by direct compression by a series of pharmacotechnical parameters. In particular, the two formulations disclosed in IT 1348011 B1 (referred herein as D1) consisting of fosfomycin trometamol and magnesium stearate were compared to three formulations which further comprised anhydrous diluents for direct compression, such as i) a combination of anhydrous calcium hydrogen phosphate and anhydrous microcrystalline cellulose; ii) anhydrous lactose and iii) anhydrous isomaltose.

The anhydrous excipients selected for blending with the active ingredient are intended to improve the direct compression of the mixture and at the same time its flow and compressibility properties. The functionality of an excipient must be evaluated in relation to an active ingredient and manufacturing process and is thus not predictable. This is particularly true in the present case wherein the content of fosfomycin trometamol is 80% or more of the final mixture thus, it is even more difficult to predict the functionality of the excipients used in the tablets of the invention since these are used in a much lower concentration than its regular use.

Material and Methods

The Active Substance:

Fosfomycin trometamol is characterized by the following critical properties:

From the point of view of chemical properties, the molecule of fosfomycin suffers a high degradation due to the presence of high humidity and temperature. The epoxide structure of the molecule has a low stability in the following way:

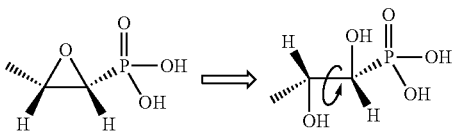

Opening ring of Fosfomycin structure.

From the point of view of pharmacotechnical properties, the initial blend has bad flowability. It was studied herein whether the additions of excipients can improve this critical parameter for the industrial process.

Manufacturing Process

The tablets were obtained by direct compression at controlled temperature of 19-22° C. and relative humidity below 20%. In particular, the manufacturing process comprised the following steps:

i. The diluents (e.g., anhydrous microcrystalline cellulose and anhydrous dibasic calcium phosphate) were sieved with a 1 mm diameter sieve and mixed for 15 minutes;

ii. Fosfomycin trometamol was sieved with 1 mm diameter sieve and mixed with the blend obtained in i) for 20 minutes;

iii. a lubricant (e.g., magnesium stearate) previously sieved with 1 mm diameter sieve was incorporated into the blender bin and mixed for 5 minutes;

iv. the blend obtained in iii) was pressed with a rotary tablet press machine with the appropriate punches according to the desired tablet form.

See FIG. 1 generally illustrating the manufacturing process. For formulations D1.1 and D1.2 the process started at ii).

Description of the Formulations Tested:

|  |  | Component | Unitari Formulation. Fosfomycin as base 1.0 g. |
|---|---|---|---|
| FORMULATION D1.1 |  |  |  |
|  |  | Fosfomycin as base | 1 |
| Fosfomycin Trometamol | 99.5 % | Fosfomycin Trometamol | 1.88 |
| Magnesium stearate | 0.5 % | Magnesium stearate | 0.01 |
|  | 100 % | Total weight per tablet (g.) | 1.89 |
| FORMULATION D1.2 |  |  |  |
|  |  | Fosfomycin as base | 1 |
| Fosfomycin Trometamol | 97.0 % | Fosfomycin Trometamol | 1.88 |
| Magnesium stearate | 3.0 % | Magnesium stearate | 0.06 |
|  | 100 % | Total weight per tablet (g.) | 1.94 |
| FORMULATION L3 |  |  |  |
|  |  | Fosfomycin as base | 1 |
| Fosfomycin Trometamol | 84.6 % | Fosfomycin Trometamol | 1.88 |
| Microcrystalline cellulose anhydrous (1.5% NMT vKFT) | 6.8 % | Microcrystalline cellulose anhydrous | 0.15 |
| Dibasic calcium phosphate, anhydrous (1.5% NMT vKFT) | 6.8 % | Dibasic calcium phosphate, anhydrous | 0.15 |
| Magnesium stearate | 1.8 % | Magnesium stearate | 0.04 |
|  | 100 % | Total weight per tablet (g.) | 2.22 |
| FORMULATION L4 |  |  |  |
|  |  | Fosfomycin as base | 1 |
| Fosfomycin Trometamol | 80.4 % | Fosfomycin Trometamol | 1.88 |
| Anhydrous Lactose (NMT 1% vKFT) | 17.9 % | Anhydrous Lactose | 0.42 |

-continued

| | | Component | Unitari Formulation. Fosfomycin as base 1.0 g. |
|---|---|---|---|
| Magnesium stearate | 1.7 % | Magnesium stearate | 0.04 |
| | 100 % | Total weight per tablet (g.) | 2.34 |
| FORMULATION L5 | | | |
| | | Fosfomycin as base | 1 |
| Fosfomycin Trometamol | 80.4 % | Fosfomycin Trometamol | 1.88 |
| Anhydrous Isomaltose (NMT 2.0% vKFT) | 17.9 % | Anhydrous Isomaltose | 0.42 |
| Magnesium stearate | 1.7 % | Magnesium stearate | 0.04 |
| | 100 % | Total weight per tablet (g.) | 2.34 |

Pharmacotechnical Parameters:

The following pharmacotechnical parameters of the powder mixture for compression were determined:
Apparent density, Da
Compacted density, Dc
Compressibility index, IC %
Haussner Index, IH
Angle of repose
Dimensional Parameters Apparent volume before sedimentation and apparent density (Da); as well as volume after sedimentation (sedimented volume) and compacted density (Dc), are important parameters due to its impact on stacking capacity and as the basis of subsequent ability to be compressed.

According to the Eur. Ph. monograph 2.9.34. *Bulk density and tapped density of powders*, the bulk density of a powder is the ratio of the mass of an untapped powder sample to its volume, including the contribution of the interparticulate void volume. Hence, the bulk density depends on both the density of powder particles and the spatial arrangement of particles in the powder bed. The bulk density is expressed in grams per millilitre despite the International Unit being kilogram per cubic metre (1 g/mL=1000 kg/m$^3$), because the measurements are made using cylinders. It may also be expressed in grams per cubic centimeter. In the present case, the bulk density of the blend was determined by measuring the volume of a known mass of powder sample in a graduated cylinder (Method 1).

According to the Eur. Ph. monograph 2.9.34. *Bulk density and tapped density of powders*, the tapped density is an increased bulk density attained after mechanically tapping a receptacle containing the powder sample. The tapped density is obtained by mechanically tapping a graduated measuring cylinder or vessel containing the powder sample. After observing the initial powder volume or mass, the measuring cylinder or vessel is mechanically tapped, and volume or mass readings are taken until little further volume or mass change is observed. In the present case, method 1 was used to determine the tapped density.

Powder flow is multifaceted and thus requires the use of multiple standardised test methods to characterise the various aspects of powder flow. The following established methods reviewed by the *European Pharmacopeia General Chapter 2.9.36 Powder Flow* were used for the powder mixture characterization:
Compressibility Parameters The simplest definition of compressibility is the ability of powder to decrease in volume under pressure. It is an indirect measure of its ability to form tablets.

The difference between the tapped density and the bulk density divided by the tapped density is the compression ratio or Carr Index:

$$\text{Compressibility Index} = 100 \times \frac{\rho_{tapped} - \rho_{bulk}}{\rho_{tapped}}$$

Flowability Parameters:

Hausner Index and angle of repose (discussed below) are important parameters due to its impact on the fluidity and gliding of the powder to be compressed.

The Hausner ratio may be calculated using measured values of bulk density (pbulk) and tapped density (ptapped) as follows:

$$\text{Hausner Ratio} = \frac{\rho_{tapped}}{\rho_{bulk}}$$

For the compressibility index and the Hausner ratio, the generally accepted scale of flowability is given in Table 2.9.36.-2 of the *European Pharmacopeia General Chapter 2.9.36*.

TABLE 2.9.36.-2

Scale of flowability[2]

| Compressibility index (per cent) | Flow character | Hausner ratio |
|---|---|---|
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very, very poor | >1.60 |

The angle of repose is the constant three-dimensional angle (relative to the horizontal base) assumed by a cone-like pile of material formed by any of several different methods, described in the *European Pharmacopeia General Chapter 2.9.36 Powder Flow* and *2.9.16 Flowability*. The angle of repose is the internal angle between the surface of the powder pile and the horizontal surface when the powders are in static equilibrium. When the powders are poured onto a horizontal surface, a conical pile and thus angle of repose will form. Angle of repose can reflect the coefficient of friction between the powder particles. The larger the angle of repose is, the larger the coefficient of friction is and the worse the flowability of the powder will be.

Optimum flowability of powders is crucial in the manufacturing process of solid single dose preparations. The European Pharmacopoeia (Ph. Eur.) therefore contains a test on "Flowability" which examines the ability of a powder to flow vertically out of a funnel. The expression of flowability in terms of time per mass may in some cases not match the macroscopic flow qualities. It is proposed the angle of repose as a better description of the flowability properties. In the present case, the angle of repose was determined according to the *European Pharmacopeia General Chapter 2.9.16 Flowability*.

While there is some variation in the qualitative description of powder flow using the angle of repose, in agreement with American pharmacopeia <1174> POWDER FLOW, much of the pharmaceutical literature appears to be consistent with the following classification:

| Flow property | Angle of repose (degrees) |
|---|---|
| Excellent | 25-30 |
| Good | 31-35 |
| Fair (aid not needed) | 36-40 |
| Passable (may hang up) | 41-45 |
| Poor (must agitate, vibrate) | 46-55 |
| Very poor | 56-65 |
| Very, very poor | >66 |

Forced Degradation Studies

Forced degradation studies of the obtained tablets comprise an exposure to the drug product at conditions more severe than accelerated conditions. It is required to provide an understanding into degradation pathways and degradation products of the drug substance and help in elucidation of the structure of the degradation products. Chemical stability of pharmaceutical molecules affects the safety and efficacy of the drug product. Moreover, knowledge of the stability of molecule helps in selecting proper formulation and package as well as providing proper storage conditions.

Analysed Stress Conditions

The different formulations were stressed at the following conditions in order to study the impurities profile. Different conditions have been checked since the best conditions has been found to appreciate how the different excipients can affect in the stability of the formulation. The final conditions which results are shown herein are the following:

Acid conditions: 100 µl of HCl 1 N has been added in a sample of each formulation (600 mg) and incubated for 20 minutes;

Basic conditions: 100 µl of NaOH 1 N has been added in a sample of each formulation (600 mg and incubated for 20 minutes Oxidative conditions: 100 µl of $H_2O_2$ 30% has been added in a sample of each formulation (600 mg and incubated for 20 minutes.

Temperature conditions: different temperatures were tested (40° C., 60° C. and 80° C.) at different exposure times.

Known Impurities of Fosfomycin Trometamol:

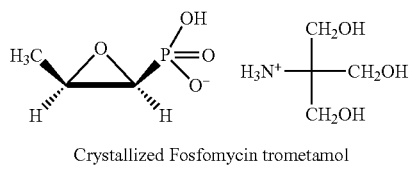

Crystallized Fosfomycin trometamol

According to *Fosfomycin Trometamol* January/2017:1425 *European Pharmacopoeia monograph*, there are four known impurities:

| Impurity | Chemical name | Structure |
|---|---|---|
| A | (1,2-dihydroxypropyl) phosphonic acid | Error! Objects cannot be created from editing field codes. |
| B | [2-[2-amino-3-hydroxy-2-(hydroxymethyl)propoxy]-1-hydroypropyl]phosphonic acid | Error! Objects cannot be created from editing field codes. |
| C | 2-amino-3-hydroxy-2-(hydroxymethyl)propyl dihydrogen phosphate (trometamol phosphoric acid monoester) | Error! Objects cannot be created from editing field codes. |
| D | [2-[[[2-[-amino-3-hydroxy-2-(hydroxymethyl)propoxy]-1-hydroxypropyl]hydroxyphosporyl]oxy]-1-hydroxypropyl]phosphonic acid (trometamyloxyfosfomycin dimmer) | Error! Objects cannot be created from editing field codes. |

The opening of the epoxide ring is referred to as Impurity A. The estimation of how the opening ring occurs has been studied for fosfomycin salts.

The rest of impurities B, C and D come from the reaction of this impurity A with the compound trometamol from different degradation mechanism. The impurity B has been obtained from the reaction between the impurity A and the molecule of trometamol at different conditions. The impurity C and D has been identified but they only appear at unusual strong degradation conditions.

*Fosfomycin Trometamol* January/2017:1425 *European Pharmacopoeia monograph* provides the experimental preparation to obtain the impurities A, B, C and D.

Analytical Method for the Known Impurities:

The solutions were prepared immediately before use and analyzed by liquid chromatography in a High Performance Liquid Chromatography equipment with a Refractive Index Detector (RID)

Test solution. Weigh a determined quantity of each formulation containing 0.600 g of the substance to be examined and dilute to 5.0 mL with the mobile phase.

Impurities solution (as described at *Fosfomycin Trometamol* January/2017:1425 *European Pharmacopoeia monograph*): Wet 0.3 g of the substance to be examined with 60 µL of purified water (water R) and heat in an oven at 60° C. for 24 h. Dissolve the residue in the mobile phase and dilute to 20.0 mL with the mobile phase (solution A). Dissolve 0.6 g of the substance to be examined in solution A and dilute to 5.0 mL with the same solution (in situ degradation to obtain impurities A, B, C and D).

Analytical Conditions:
  Column: size: I=0.25 m, Ø=4.6 mm, and stationary phase: aminopropylsilyl silica gel for chromatography R (5 μm).
  Mobile phase: 10.89 g/L solution of potassium dihydrogen phosphate R in water for chromatography R.
  Flow rate: 1.0 mL/min.
  Detection: differential refractometer at 35° C.
  Injection: 10 μL of the test solution and reference solutions.
  Run time: twice the retention time of fosfomycin.
  Relative retention with reference to fosfomycin (retention time=about 9 min): trometamol (2 peaks)=about 0.3; impurity B=about 0.48; impurity C=about 0.54; impurity A=about 0.88; impurity D=about 1.27.

Results 1.1. Pharmacotechnical Parameters:

TABLE 1

Summary of the tested pharmacotechnical parameters of the mixture for compression.

|  | FORMULATION D1.1 | FORMULATION D1.2 | FORMULATION L3 | FORMULATION L4 | FORMULATION L5 |
|---|---|---|---|---|---|
| Apparent density, Da (g/mL) | 0.448 | 0.480 | 0.571 | 0.446 | 0.508 |
| Compacted density, Dc (g/mL) | 0.718 | 0.701 | 0.709 | 0.676 | 0.686 |
| Compressibility index, CI (%) | 37.50 | 31.58 | 19.57 | 33.93 | 26.00 |
| Haussner Index, IH | 1.60 | 1.46 | 1.24 | 1.51 | 1.35 |
| Angle of repose (°) | 34.24 | 35.08 | 29.77 | 36.50 | 32.37 |

Legend: For CI (%) and HR Excellent to Fair properties are indicated in bold letters and poor to very poor properties have been underlined. For angle of repose, excellent properties are highlighted in bold. It shows the mean of the results in experiments conducted by duplicate.

Table 1: Summary of the tested pharmacotechnical parameters of the mixture for compression. Legend: For CI (%) and HR Excellent to Fair properties are indicated in bold letters and poor to very poor properties have been underlined. For angle of repose, excellent properties are highlighted in bold. It shows the mean of the results in experiments conducted by duplicate.

On the basis of the CI (%) and HR, the flowability properties of formulation L3 were fair conversely these were poor to very poor for the formulations of D1 and poor when using other anhydrous diluents. When considering the angle of repose values, the flowing properties of formulation L3 were excellent whilst for the rest of compositions were between fair and poor. According to the obtained results, the compressibility index, the Haussner index and the angle of repose are significantly better for the formulation L3. Thus, the powder of formulation L3 has superior compressibility and flowability properties, with respect to the formulations described in D1 but also in comparison with formulations using other anhydrous diluents.

1.2. Stability Results: Forced Degradation Studies

As described under Material and Methods above, the different formulations were subjected to forced degradation assays in order to study the profile of impurities:

The tables below summarize the obtained results regarding the presence of impurities A and B with regard to the acidic, basic and oxidative conditions. No relevant results were found for the degradation at different temperatures. At higher temperatures (80° C.), the fosfomycin molecule suffered a complete degradation and it was not possible to evaluate any difference between formulations. At lower temperatures (40° C.), no degradation was observed or the degradation occurred at the same level for the different formulations.

|  | FORMULATION D1.1 | FORMULATION D1.2 | FORMULATION L3 | FORMULATION L4 | FORMULATION L5 |
|---|---|---|---|---|---|
| % Impurity A | | | | | |
| Initial Conditions | 0.19 | 0.12 | 0.04 | 0.06 | 0.05 |
| HCl 1M for 24 hours | 0.86 (4.5 fold increase) | 0.82 (6.8 fold increase) | 0.04 | 0.80 (13.33 fold increase) | 0.61 (12.2 fold increase) |
| NaOH 1M for 24 hours | 0.02 | 0.06 | 0.03 | 0.06 | 0.06 |
| $H_2O_2$ for 24 hours | 0.08 | 0.08 | 0.09 | 0.12 | 0.14 |
| % Impurity B | | | | | |
| Initial Conditions | 0.04 | 0.06 | 0.05 | 0.06 | 0.06 |
| HCl 1M for 24 hours | 0.05 | 0.06 | 0.05 | 0.06 | 0.09 |
| NaOH 1M for 24 hours | 0.04 | 0.04 | 0.05 | 0.05 | 0.07 |
| $H_2O_2$ 1M for 24 hours | 0.04 | 0.05 | 0.06 | 0.11 | 0.07 |

Accordingly, significant differences were found between the formulations with regard to impurity A under acidic conditions. It was strikingly found that for all formulations other than L3, the levels of impurity A were superior to 0.3%. Accordingly, the levels of impurity A were significantly superior to the established limit for the shelf-life specification.

The components of the formulation L3 were found to improve the chemical stability of the fosfomycin molecule at acidic conditions. An advantage associated to having a formulation stable under acidic conditions is that it will not require a gastro-resistant coating to avoid degradation in the stomach. The chromatograms corresponding to the degradation assays of the 5 formulations are provided as FIGS. 2 to 6.

No relevant differences have been obtained for the rest of tested conditions.

Example 2.—Optimizing the Excipients Composition

Material and Methods

The following formulations comprising microcrystalline cellulose and calcium hydrogen phosphate were assayed in order to determine the optimal concentration of excipients on the basis of the pharmacotechnical properties of the powder.

Proposals 1, 2 and 3 had an increasing amount of flavouring agent, namely about 5%, 10% and 15% respectively. Also, from each of the proposals a version 0.1, 0.2 and 0.3 was assayed comprising increasing amounts of microcrystalline cellulose.

Description of the Formulations Tested:

Excipients Optimization.—Reduction of Excipients Concentration

Unitary Formula

|  | Proposal 1.1 | | Proposal 1.2 | | Proposal 1.3 | |
| --- | --- | --- | --- | --- | --- | --- |
| FosfomycinTrometamol | 1877 | 80.40% | 1877 | 75.55% | 1877 | 71.25% |
| Magnesium Stearate | 40.5 | 1.73% | 40.5 | 1.63% | 40.5 | 1.54% |
| Anhydrous Microcrystalline Cellulose | 150 | 6.43% | 300 | 12.07% | 450 | 17.08% |
| Anhydrous Calcium Hydrogen Phosphate | 150 | 6.43% | 150 | 6.04% | 150 | 5.69% |
| Beef flavour Aroma PC 0125 | 117 | 5.01% | 117 | 4.71% | 117 | 4.44% |
| Tablet weight | 2334.5 | 100.00% | 2484.5 | 100.00% | 2634.5 | 100.00% |

Unitary Formula

|  | Proposal 2.1 | | Proposal 2.2 | | Proposal 2.3 | |
| --- | --- | --- | --- | --- | --- | --- |
| FosfomycinTrometamol | 1877 | 76.16% | 1877 | 71.79% | 1877 | 64.40% |
| Magnesium Stearate | 40.5 | 1.64% | 40.5 | 1.55% | 40.5 | 1.39% |
| Anhydrous Microcrystalline Cellulose | 150 | 6.09% | 300 | 11.47% | 450 | 15.44% |
| Anhydrous Calcium Hydrogen Phosphate | 150 | 6.09% | 150 | 5.74% | 300 | 10.29% |
| Beef flavor Aroma PC 0125 | 247 | 10.02% | 247 | 9.45% | 247 | 8.47% |
| Tablet weight | 2464.5 | 100.00% | 2614.5 | 100.00% | 2914.5 | 100.00% |

Unitary Formula

|  | Proposal 3.1 | | Proposal 3.2 | | Proposal 3.3 | |
| --- | --- | --- | --- | --- | --- | --- |
| FosfomycinTrometamol | 1877 | 71.93% | 1877 | 68.02% | 1877 | 61.35% |
| Magnesium Stearate | 40.5 | 1.55% | 40.5 | 1.47% | 40.5 | 1.32% |
| Anhydrous Microcrystalline Cellulose | 150 | 5.75% | 300 | 10.87% | 450 | 14.71% |
| Anhydrous Calcium Hydrogen Phosphate | 150 | 5.75% | 150 | 5.44% | 300 | 9.81% |
| Beef flavour Aroma PC 0125 | 392 | 15.02% | 392 | 14.21% | 392 | 12.81% |
| Tablet weight | 2609.5 | 100.00% | 2759.5 | 100.00% | 3059.5 | 100.00% |

Results

1. Pharmacotechnical Properties of the Obtained Mixtures:

The characterization of the powder is carried out for assessing the parameters of the mixture for compression.

|  | Proposal 1.1 | Proposal 1.2 | Proposal 1.3 |
|---|---|---|---|
| angle of repose | 28 | 24 | 25 |
| sliding time (s) | 8 | 9 | 8 |

|  | Proposal 2.1 | Proposal 2.2 | Proposal 2.3 |
|---|---|---|---|
| angle of repose | 20 | 21 | 21 |
| sliding time (s) | 7 | 7 | 6 |

|  | Proposal 3.1 | Proposal 3.2 | Proposal 3.3 |
|---|---|---|---|
| angle of repose | 19 | 17 | 15 |
| sliding time (s) | 5 | 5 | 4 |

The impact of the angle of repose on the flowing properties has been defined above. Also, the lower the sliding time, the better the flowing properties.

In agreement with the angle of repose and gliding time for all the tested proposals (1, 2, 3), the reduction in the amount of microcrystalline cellulose did not involve a loss of flowing properties.

The evaluation of the mixtures based on the parameters of angle of repose and sliding time supports that it is possible to reduce the excipient concentration by 20-30% (depending on the aroma concentration) while maintaining a mixture of appropriate pharmacotechnical properties for its correct compression.

Overall, from the tested formulations, the compositions with 5% flavour (Proposal 1) were preferred on the basis of its increased acceptance by dogs in a palatability assay (data not shown) and, from these, Proposal 1.1 was found to be preferred on the basis of its lower content of microcrystalline cellulose, thus providing a tablet with a lower total weight.

Example 3—Further Pharmacotechnical Characterization of the Tablets of the Invention Tablets of fosfomycin trometamol, 1000 mg of FOS base were manufactured by direct compression as described under Example 1. Said dose would be between the doses of 250 and 1400 mg of fosfomycin base identified in preliminary pharmacokinetic analysis as ideal doses for cats and dogs, respectively, so it would collect intermediate properties at both doses and would help us to extrapolate the study to both doses. This premise will be used for the analytical validation and manufacturing process phases carried out later.

The following galenic batches were prepared at different aroma concentrations:

|  | Batch: 17.099 (5% beef aroma) | Batch: 17.100 (10% beef aroma) | Batch: 17.101 (15% beef aroma) |
|---|---|---|---|
| FosfomycinTrometamol | 1877 (80.4%) | 1877 (76.16%) | 1877 (71.93%) |
| Magnesium Stearate | 40.5 (1.73%) | 40.5 (1.64%) | 40.5 (1.55%) |
| Anhydrous Microcrystalline Cellulose | 150 (6.43%) | 150 (6.09%) | 150 (5.75%) |
| Anhydrous Calcium Hydrogen Phosphate | 150 (6.43%) | 150 (6.09%) | 150 (5.75%) |
| Beef flavour Aroma PC 0125 | 117 (5.01%) | 247 (10.02%) | 392 (15.01%) |
| Tablet weight | 2334.5 mg. | 2464.5 mg | 2609.5 mg |

Physical Parameters of the Tablets

The mean values for the following parameters were as follows:

|  | Hardness (N) | Friability (%) | Weight (mg) |
|---|---|---|---|
| Guide values | To be determined | <1% | 2817-3113<br>2979-3293<br>3148-3480 |
| Batch: 17.099 | 52 | 0.3 | 2963 |
| Batch: 17.100 | 48 | 0.4 | 3132 |
| Batch: 17.101 | 57 | 0.2 | 3310 |

Hardness was determined using a durometer as defined in as the (Ph. Eur. 2.9.8—resistance to crushing strength).

Tablet friability test was conducted as described in Ph. Eur. 2.9.7.

Appearance

Figure 7:
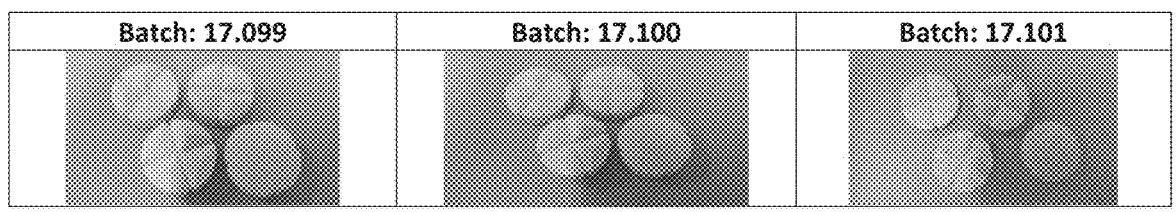
FIG. 7. Photographs of the batches 17.099, 17.100, 17.101 showing the appearance of the obtained tablets with a break mark.

All tablets have a correct appearance as shown in FIG. 7.

The invention claimed is:

1. An oral pharmaceutical composition in tablet form comprising:
   a. fosfomycin trometamol;
   b. anhydrous calcium hydrogen phosphate; and
   c. anhydrous microcrystalline cellulose.

2. The oral composition according to claim 1, wherein said composition comprises:
   a. from 80% to 95% w/w of fosfomycin trometamol; and
   b. from 5% to 20% w/w of a combination of anhydrous calcium hydrogen phosphate and anhydrous microcrystalline cellulose.

3. The oral composition according to claim 1, wherein said composition comprises from 5 to 10% w/w of anhydrous calcium hydrogen phosphate and 5 to 10% w/w of anhydrous microcrystalline cellulose.

4. The oral composition according to claim 1, wherein anhydrous calcium hydrogen phosphate and anhydrous microcrystalline cellulose are found at a 2:1 to 1:2 ratio.

5. The oral composition according to claim 1, wherein the content of fosfomycin base is of at least 250 mg.

6. The oral composition according to claim 1, wherein the total weight of the tablets is from 2000 mg to 3500 mg.

7. The oral composition according to claim 1, wherein said tablet is a tablet with a break mark.

8. The oral composition according to claim 1, wherein said tablet is obtained by direct compression.

9. A method of manufacturing the tablet composition as defined in claim 1, which comprises the steps of:

i. mixing anhydrous calcium hydrogen phosphate with anhydrous microcrystalline cellulose and with fosfomycin trometamol; and
ii. pressing the blend obtained in i) with a tablet press machine and thereby obtaining the tablets.

10. The oral composition according to claim 1 further comprising a lubricant.

11. The oral composition according to claim 10, wherein said lubricant is a stearic acid or a stearic acid metal salt.

12. The oral composition according to claim 10, wherein said lubricant is magnesium stearate.

13. The oral composition according to claim 12, wherein said composition comprises:
   a. from 80% to 85% w/w of fosfomycin trometamol;
   b. from 5% to 10% w/w of anhydrous microcrystalline cellulose;
   c. from 5% to 10% w/w of anhydrous dibasic calcium phosphate
   d. from 1.5% to 2.5% w/w of magnesium stearate; and
   e. from 0% to 15% w/w of a flavoring agent.

14. The oral composition according to claim 10, further comprising other pharmaceutically acceptable excipients.

15. The oral composition according to claim 10, wherein said composition comprises:
   a. from 80% to 95% w/w of fosfomycin trometamol;
   b. from 5% to 20% w/w of a combination of anhydrous calcium hydrogen phosphate and anhydrous microcrystalline cellulose; and
   c. from 0.1% to 3% w/w of a lubricant.

16. The oral composition according to claim 14, wherein said composition comprises:
   a. from 80% to 95% w/w of fosfomycin trometamol;
   b. from 5% to 20% w/w of a combination of anhydrous calcium hydrogen phosphate and anhydrous microcrystalline cellulose;
   c. from 0.1% to 3% w/w of a lubricant; and
   d. other pharmaceutically acceptable excipients in quantity enough to complete the 100% of the composition total weight.

17. The oral composition according to claim 1, wherein anhydrous calcium hydrogen phosphate and anhydrous microcrystalline cellulose are found at a 1:1 ratio.

18. The oral composition according to claim 1, wherein said composition consists of:
   a. 84.6% w/w of fosfomycin trometamol;
   b. 6.8% w/w of anhydrous microcrystalline cellulose;
   c. 6.8% w/w of anhydrous dibasic calcium phosphate; and
   d. 1.8% w/w of magnesium stearate.

19. The method of manufacturing of claim 9, comprising the steps of:
   i. mixing anhydrous calcium hydrogen phosphate with anhydrous microcrystalline cellulose and with fosfomycin trometamol;
   ii. mixing a lubricant with the blend obtained in i); and
   iii. pressing the blend obtained in ii) with a tablet press machine and thereby obtaining the tablets.

* * * * *